(12) United States Patent
Roehrlein et al.

(10) Patent No.: US 10,406,372 B2
(45) Date of Patent: Sep. 10, 2019

(54) HEADPIECELESS HEARING ASSISTANCE APPARATUS, SYSTEMS AND METHODS WITH DISTRIBUTED POWER

(71) Applicant: Advanced Bionics AG, Staefa (CH)

(72) Inventors: Gerhard Roehrlein, Staefa (CH); Stefan Launer, Zurich (CH); Lee F. Hartley, Valencia, CA (US); Lakshmi Mishra, Carlsbad, CA (US); Abhijit Kulkarni, Newbury Park, CA (US); Mark Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/125,153

(22) PCT Filed: Mar. 22, 2014

(86) PCT No.: PCT/US2014/031529
§ 371 (c)(1),
(2) Date: Sep. 10, 2016

(87) PCT Pub. No.: WO2015/147774
PCT Pub. Date: Oct. 1, 2015

(65) Prior Publication Data
US 2017/0028199 A1 Feb. 2, 2017

(51) Int. Cl.
*A61N 1/372* (2006.01)
*A61N 1/378* (2006.01)
*A61N 1/05* (2006.01)
*H04R 25/00* (2006.01)
*A61N 1/36* (2006.01)

(52) U.S. Cl.
CPC ....... *A61N 1/37229* (2013.01); *A61N 1/0541* (2013.01); *A61N 1/36036* (2017.08); *A61N 1/3787* (2013.01); *A61N 1/37211* (2013.01); *H04R 25/554* (2013.01); *H04R 25/602* (2013.01); *H04R 25/606* (2013.01); *H04R 2225/021* (2013.01); *H04R 2225/51* (2013.01)

(58) Field of Classification Search
CPC .............. A61N 1/37229; H04R 25/554; H04R 2225/021; H04R 25/04; H04R 25/00
See application file for complete search history.

(56) References Cited

U.S. PATENT DOCUMENTS

| | | | |
|---|---|---|---|
| 4,918,745 A | 4/1990 | Hitchison |
| 5,751,820 A | 5/1998 | Taenzer et al. |
| 5,824,022 A | 10/1998 | Zilberman et al. |
| 6,775,389 B2 | 8/2004 | Harrison et al. |

(Continued)

FOREIGN PATENT DOCUMENTS

| | | |
|---|---|---|
| WO | WO2013008057 | 1/2013 |
| WO | WO2013116161 | 8/2013 |

(Continued)

OTHER PUBLICATIONS

PCT International Search and Written Opinion dated Jul. 14, 2014 for PCT App. Ser. Appl. No. PCT/US2014/031529.

(Continued)

*Primary Examiner* — Joseph M Dietrich
(74) *Attorney, Agent, or Firm* — Henricks Slavin LLP

(57) ABSTRACT

Hearing assistance apparatus, systems and methods that involve the use of distributed power without the use of a headpiece.

19 Claims, 7 Drawing Sheets

(56) References Cited

U.S. PATENT DOCUMENTS

| | | |
|---|---|---|
| 6,842,647 B1 | 1/2005 | Griffith |
| 7,003,353 B1 | 2/2006 | Parkhouse |
| 7,039,466 B1 | 5/2006 | Harrison et al. |
| 7,450,994 B1 | 11/2008 | Mishra et al. |
| 7,599,508 B1 | 10/2009 | Lynch et al. |
| 8,027,733 B1 | 9/2011 | Fridman et al. |
| 8,073,171 B2 | 12/2011 | Haenggi et al. |
| 8,270,647 B2 | 9/2012 | Crawford et al. |
| 8,515,112 B2 | 8/2013 | Crawford et al. |
| 8,811,643 B2 | 8/2014 | Crawford et al. |
| 8,983,102 B2 | 3/2015 | Crawford et al. |
| 9,392,384 B2 | 7/2016 | Crawford et al. |
| 9,968,781 B2 | 5/2018 | Roehrlein et al. |
| 10,195,444 B2 | 2/2019 | Roehrlein et al. |
| 2003/0171787 A1 | 9/2003 | Money et al. |
| 2004/0172102 A1 | 9/2004 | Leysieffer |
| 2005/0159791 A1 | 7/2005 | Daly et al. |
| 2005/0209657 A1 | 9/2005 | Chung et al. |
| 2006/0190059 A1 | 8/2006 | Griffith |
| 2007/0027676 A1 | 2/2007 | Chambers et al. |
| 2007/0282394 A1 | 12/2007 | Segel et al. |
| 2008/0002834 A1 | 1/2008 | Hochmair |
| 2008/0177353 A1 | 7/2008 | Hirota et al. |
| 2008/0300658 A1 | 12/2008 | Meskens |
| 2009/0216296 A1 | 8/2009 | Meskens |
| 2009/0292338 A1 | 11/2009 | Gordon et al. |
| 2010/0046778 A1 | 2/2010 | Crawford et al. |
| 2010/0198303 A1 | 8/2010 | Haller et al. |
| 2010/0280307 A1 | 11/2010 | Lineaweaver et al. |
| 2010/0329491 A1 | 12/2010 | Johansen |
| 2012/0041515 A1* | 2/2012 | Meskens ............ A61N 1/37229 607/57 |
| 2012/0109297 A1* | 5/2012 | Van den Heuvel ......................... A61N 1/36032 623/10 |
| 2012/0150259 A1 | 6/2012 | Meskens |
| 2012/0316618 A1 | 12/2012 | Zierhofer et al. |
| 2013/0006327 A1 | 1/2013 | Mishra et al. |
| 2013/0066398 A1 | 3/2013 | Duftner et al. |
| 2014/0025138 A1 | 1/2014 | Meskens et al. |
| 2014/0064528 A1 | 3/2014 | Flood et al. |
| 2015/0224312 A1* | 8/2015 | Platz .................. A61N 1/36032 607/57 |
| 2016/0375242 A1 | 12/2016 | Roehrlein et al. |
| 2016/0375243 A1 | 12/2016 | Roehrlein et al. |

FOREIGN PATENT DOCUMENTS

| | | |
|---|---|---|
| WO | WO2014003777 | 1/2014 |
| WO | WO2014035379 | 3/2014 |
| WO | WO2014035592 A1 | 3/2014 |

OTHER PUBLICATIONS

Communication under Rule 71(3) dated Sep. 3, 2018 in EPO application serial No. 14 717 970.9.

* cited by examiner

FIG. 1 - Prior Art

HEADPIECELESS HEARING ASSISTANCE APPARATUS, SYSTEMS AND METHODS WITH DISTRIBUTED POWER

CROSS-REFERENCE TO RELATED APPLICATIONS

This application is the U.S. National Stage of PCT App. Ser. No. PCT/US2014/031529, filed Mar. 22, 2014.

BACKGROUND

1. Field

The present disclosure relates generally to hearing assistance devices such as, for example, implantable cochlear stimulation ("ICS") systems and hearing aids.

2. Description of the Related Art

A wide variety of hearing assistance devices are available. Such devices include, but are not limited to, ICS systems and hearing aids.

ICS systems are used to help the profoundly deaf perceive a sensation of sound by directly exciting the auditory nerve with controlled impulses of electrical current. Ambient sound pressure waves are picked up by an externally worn microphone and converted to electrical signals. The electrical signals, in turn, are processed by sound processor circuitry, converted to stimulation data (e.g., a pulse sequence having varying pulse widths and/or amplitudes), and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. Alternatively, the implantable electrode array may be directly inserted into the cochlear nerve without residing in the cochlea.

Referring to FIG. 1, conventional ICS systems commonly include an implantable device 11 and an external sound processor 12 with a housing 14, sound processor circuitry 16, a microphone 18 that is in communication with the sound processor circuitry, and a battery or other power supply 20. In the type of ICS system illustrated in FIG. 1, the sound processor is worn behind the ear (a "BTE sound processor") and includes an earhook 22. The sound processor 12 transmits stimulation data, as well as power from its power supply 20, to the implantable device 11 by way of an inductive link. To that end, ICS systems include a headpiece 24 that is connected to the sound processor 12 by a cable 26, and the implantable device 11 has a positioning magnet (not shown) that keeps the headpiece properly positioned relative to the implantable device. The headpiece 24 has a coil antenna that is used to connect the headpiece (and BTE sound processor by way of the headpiece) to the implantable device via an inductive link. So configured, the BTE sound processor provides sound processing functionality and also provides power for the entire ICS system. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor. Other ICS systems are configured such that all of the external components (e.g., the battery, the microphone, the sound processor, and the coil) are carried within a single headpiece. One example of such a system is disclosed in U.S. Pat. Pub. No. 2010/0046778, which is entitled "Integrated Cochlear Implant Headpiece" and incorporated herein by reference in its entirety.

Hearing aids include a microphone, sound processor circuitry, and a speaker (sometimes referred to as a "receiver"). Here too, ambient sound pressure waves are picked up by the microphone and converted into electrical signals. The electrical signals, in turn, are processed by sound processor circuitry. The processed signals drive the speaker, which delivers amplified (or otherwise processed) sound pressure waves to the ear canal. Exemplary types of hearing aids include, but are not limited to, BTE hearing aids, receiver-in-canal ("RIC") hearing aids, in-the-canal ("ITC") hearing aids and completely in-the-canal ("CIC") hearing aids. Examples of commercially available hearing aids include, but are not limited to, the Phonak™ Ambra™ hearing aid and the Phonak™ Naida™ hearing aid.

The present inventors have determined that conventional ICS systems are susceptible to improvement. For example, the present inventors have determined that some patients would benefit from an ICS system with an external sound processor that is smaller and lighter than those currently available and that this may be accomplished by altering the manner in which power is stored and supplied within the ICS system. The present inventors have determined that some patients would prefer an ICS system without a headpiece.

SUMMARY

A hearing assistance system in accordance with one of the present inventions includes an implantable cochlear stimulator with a battery, a hearing assistance device with a battery, sound processor circuitry that converts electrical signals from a microphone into stimulation data, and a data communication apparatus configured to wirelessly transmit the stimulation data, and a retransmission apparatus, with a data communication apparatus, that wirelessly receives the stimulation data and wirelessly transmits the stimulation data to the implantable cochlear stimulator. The system does not include a headpiece.

A hearing assistance system in accordance with one of the present inventions includes an implantable cochlear stimulator with a battery, a hearing assistance device, with a battery, a microphone that converts sound pressure waves into electrical signals, and data communication apparatus that wirelessly transmits the electrical signals, and a retransmission apparatus, with a data communication apparatus and sound processor circuitry, that wirelessly receives electrical signals from the hearing assistance device, converts the electrical signals from a microphone into stimulation data, and wirelessly transmits the stimulation data to the implantable cochlear stimulator. The system does not include a headpiece.

A method in accordance with one of the present inventions includes the steps of wirelessly transmitting stimulation data from an external hearing assistance device associated with the user's head to a retransmission apparatus that is not a head-mounted device, and wirelessly transmitting the stimulation data from the retransmission apparatus to a cochlear stimulator that does not include a sound processor and is implanted within the user's head. The method does not involve the use of a headpiece.

A method in accordance with one of the present inventions includes the steps of wirelessly transmitting microphone-generated signals from an external hearing assistance device associated with the user's head to a retransmission apparatus that is not a head-mounted device, converting the microphone-generated signals into stimulation data with the retransmission apparatus, and wirelessly transmitting the stimulation data from the retransmission apparatus to a cochlear stimulator that does not include a sound processor and is implanted within the user's head. The method does not involve the use of a headpiece.

A hearing assistance system in accordance with one of the present inventions includes an implantable cochlear stimulator with a battery, a position element, a power receiver apparatus, an electrode array, a stimulation data receiver apparatus, and a stimulation processor, an external hearing assistance device with a battery, sound processor circuitry that converts electrical signals from a microphone into stimulation data, and a data communication apparatus configured to wirelessly transmit the stimulation data, and a head mountable power supply with a battery, a magnet that is magnetically attracted to the position element, and a power transmission apparatus operably connected to the battery and configured to wirelessly supply power to the implantable cochlear stimulator power receiver apparatus. The implantable cochlear stimulator is operable in a first stimulation mode that is powered by the implantable cochlear stimulator battery and is also operable in a second stimulation mode that is powered by the head mountable power supply battery.

There are a number of advantages associated with such systems and methods. For example, an implanted cochlear stimulator with its own battery facilitates a reduction in the size/weight of the external hearing assistance device (e.g., a BTE sound processor) by an amount that was heretofore attributable to the supply of power to the cochlear stimulator. The use of a retransmission apparatus reduces the transmission-related power requirements of the external hearing assistance device (e.g., a BTE sound processor) and, in some instances provides sound processing functionality, which also facilitates a reduction in the size/weight of the external hearing assistance device. The present apparatus, systems and method may also be implemented in electric acoustic stimulation ("EAS") systems where a hearing aid and a cochlear implant are used together in the same ear. Systems including the head mountable power supply can operate despite the fact that the implantable cochlear stimulator battery is not functioning properly.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions have application in a wide variety of hearing assistance devices and systems that provide sound (i.e., either sound or a perception of sound) to the hearing impaired as well as others who require such hearing devices on a situational basis. Examples of such hearing assistance devices and systems include hearing aids and ICS systems where an external sound processor communicates with a cochlear implant. The present inventions are not, however, limited to such devices and systems and may be employed in combination with other hearing assistance devices and systems that currently exist, or are yet to be developed.

Figure 1:
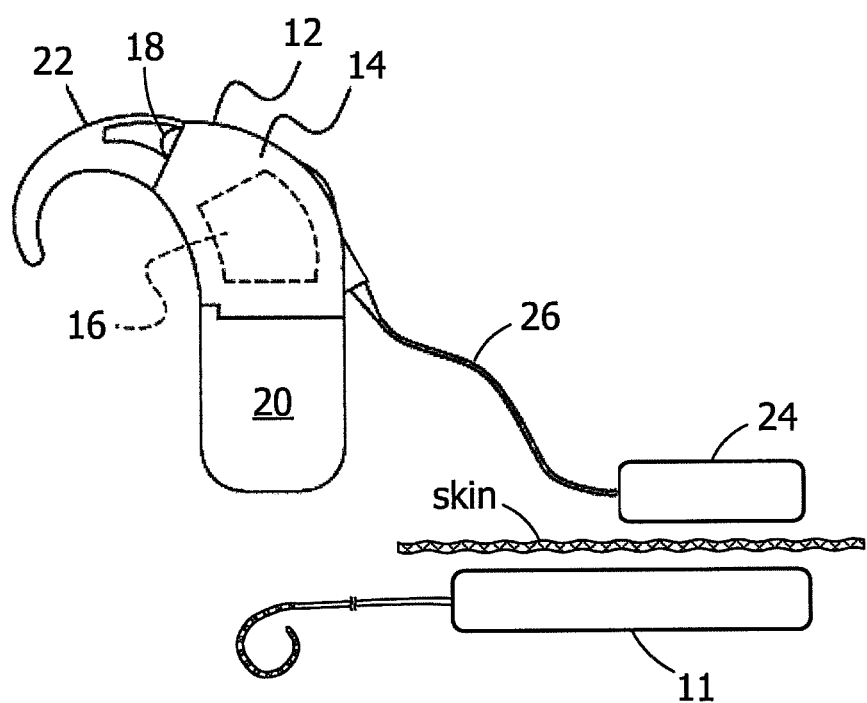
FIG. 1 is a side view of a conventional ICS system with a BTE sound processor, a headpiece and a cochlear implant.
Figure 2:
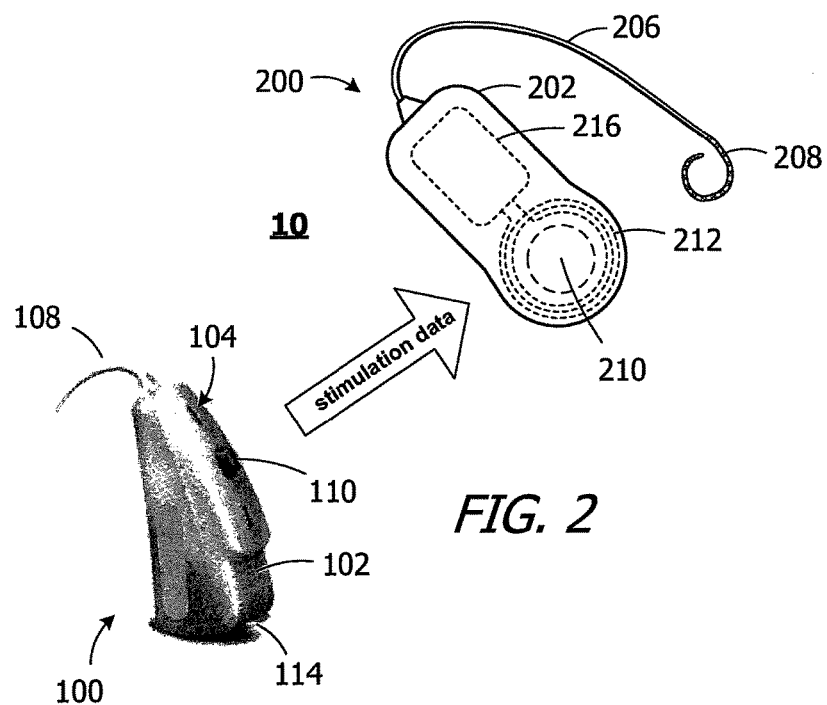
FIG. 2 is a plan view showing components of an ICS system in accordance with one embodiment of a present invention.

One example of a hearing assistance system is the ICS system generally represented by reference numeral 10 in FIG. 2. The exemplary ICS system 10 includes an external BTE hearing assistance device 100 and an implantable cochlear simulator 200. The system does not include a headpiece. Briefly, the hearing assistance device 100 supplies stimulation data, but not power, to the cochlear simulator 200 by way of a wireless link. The cochlear simulator 200 is powered by its own battery.

Figure 3:
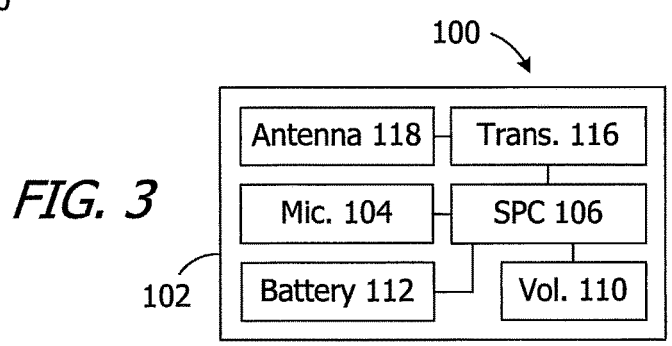
FIG. 3 is a block diagram of a hearing assistance device in accordance with one embodiment of a present invention.

Referring also to FIG. 3, the exemplary BTE hearing assistance device 100 includes a housing 102, a microphone 104, sound processor circuitry ("SPC") 106, and a retention member 108. A speaker (not shown) may be provided in some implementations. A volume control button 110 is positioned on the exterior of the housing 102. The hearing assistance device 100 also includes a battery or other power supply 112 that supplies power to the sound processor circuitry 106 and other power consuming components of the BTE hearing assistance device. In the illustrated implementation, the power supply 112 is carried by a removable battery holder (not shown) that is secured to housing 102 with a latch 114. In other implementations, a rechargeable battery may be a permanently housed within the hearing aid and the battery holder may be omitted. Such a hearing aid may be placed in a battery charger as necessary.

There is also a wireless data link between the BTE hearing assistance device 100 and the cochlear simulator 200. In the illustrated embodiment, a data transmitter 116 drives a data antenna 118 to transmit stimulation data, but not power, to the cochlear simulator 200. The BTE hearing assistance device 100 does not supply power to the cochlear simulator 200. The data transmitter 116 and data antenna 118 are collectively referred to as a data communication apparatus and, in those implementations where the BTE hearing assistance device wirelessly receives information (e.g., where status information is transmitted from the cochlear simulator 200 to the BTE hearing assistance device 100), the data communication apparatus would include a data transceiver and a data antenna. One example of a suitable data communication apparatus is a near field magnetic induction ("NFMI") apparatus where a data transmitter and coil antenna generate a short range, low-power, non-propagating magnetic field. Other types of wireless links, including but not limited to RF data communication apparatus, may also be employed to transmit stimulation data from the hearing assistance device 100 to the cochlear simulator 200.

Figure 4:
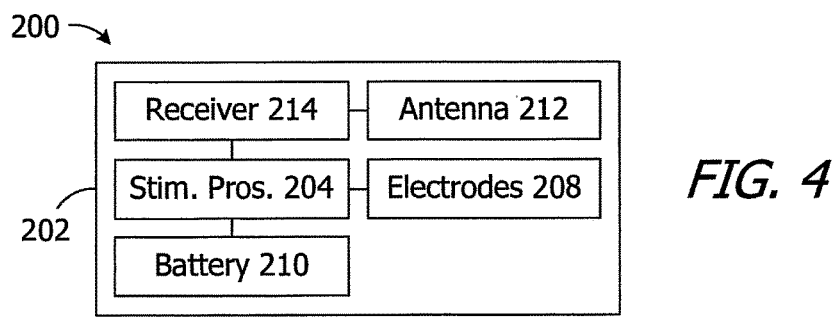
FIG. 4 is a block diagram of an implantable cochlear stimulator in accordance with one embodiment of a present invention.

As illustrated in FIGS. 2 and 4, the exemplary cochlear stimulator 200 includes a flexible housing 202 formed from a silicone elastomer or other suitable material, an internal stimulation processor 204, a cochlear lead 206 with an electrode array 208, and a battery 210, such as a high energy primary battery or a rechargeable battery. The cochlear stimulator 200 also includes data receiver apparatus which, in the illustrated implementation, consists of an antenna 212 and a receiver 214. The stimulation processor 204 and receiver 214 may be located on a common circuit board 216, or on separate boards. The antenna and receiver 212 and 214 receive stimulation data from the hearing assistance device 100. The stimulation data is generated by the hearing assistance device 100 and is transmitted to the cochlear stimulator 200. The antenna 214 may be a coil antenna that is inductively coupled to the coil antenna 118 of the hearing assistance device 100. The data receiver apparatus may be, for example, an NFMI data receiver apparatus or an RF data receiver apparatus. Additionally, given that the system 10 does not include a headpiece, the cochlear stimulator 200 need not include a positioning magnet or other positioning element that maintains alignment between the cochlear stimulator and a headpiece, the illustrated embodiment does not include such a magnet or other positioning element. There may, however, be instances where such positioning is useful and, accordingly, other embodiments of the cochlear stimulator 200 may include a positioning magnet or other positioning element. One example of a system that includes a cochlear stimulator with a positioning magnet is discussed below with reference to FIGS. 13-16.

In those instances where the battery 210 is a rechargeable battery, the cochlear stimulator 200 may be provided with power receiver apparatus. Power may be received by way of the coil antenna 212 or by way of a separate antenna. Here, power from an external inductive recharging apparatus (not shown) may be supplied to the battery 210 as necessary.

As used herein, a "stimulation processor" is a processor that converts the stimulation data from a sound processing device (e.g., the sound processor circuitry 106) into stimulation signals that stimulate the electrodes of an electrode array (e.g., the electrodes in array 208). A "stimulation processor" does not itself convert electrical signals from a microphone into stimulation data and, therefore, is not a "sound processor." It should also be noted that the exemplary implantable cochlear stimulator 200 is not a totally implantable cochlear implant system, nor is it part of such a system. To that end, the cochlear stimulator 200 does not include a microphone or sound processor circuitry. The cochlear stimulator 200 relies on another device (here, the BTE hearing assistance device 100) for microphone and sound processing functionality.

Figure 5:
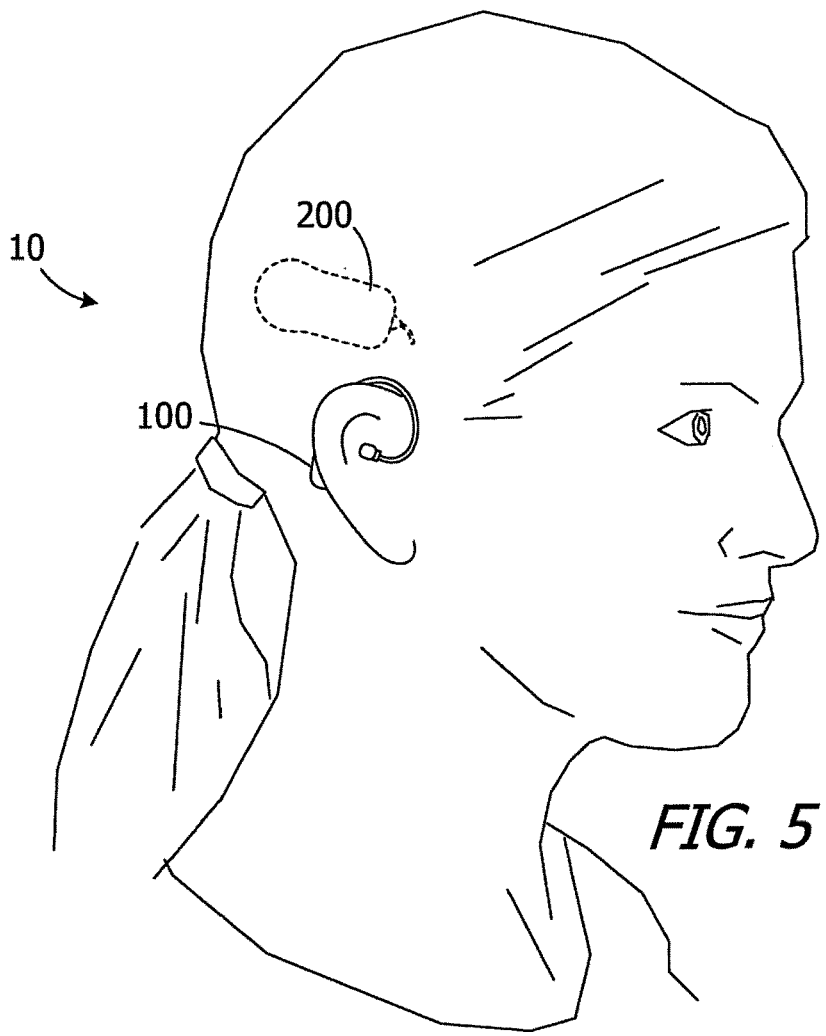
FIG. 5 is a side view showing the ICS system as illustrated in FIGS. 2-4 in use.

During use of the exemplary system 10, and as illustrated in FIG. 5, the BTE hearing assistance device 100 is positioned behind the ear. There is a direct wireless communication between BTE hearing assistance device 100 and the cochlear stimulator 200. The hearing assistance device 100 and cochlear stimulator 200 are each powered by their own respective batteries 112 and 210. The hearing assistance device microphone 104 picks up ambient sound pressure waves and converts them into electrical signals. The electrical signals are the processed by the sound processor circuitry 106 and converted to stimulation data (e.g., a pulse sequence having varying pulse widths and/or amplitudes). The hearing assistance device data transmitter 116 and antenna 118 establish a wireless link with the antenna 212 and receiver 214, so that the hearing assistance device 100 can transmit stimulation data, but not power, to the cochlear stimulator. The stimulation processor 204 converts the data into stimulation signals that stimulate the electrodes in the array 208. The electrode array 208 electrically stimulates the auditory nerve, thereby providing the user with sensory input that is a representation of external sound waves which were sensed by the microphone 104.

Figure 6:
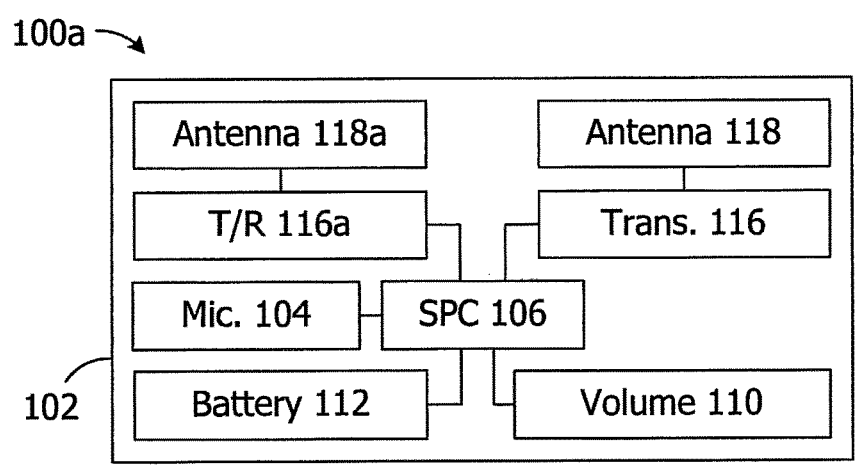
FIG. 6 is a block diagram of a hearing assistance device in accordance with one embodiment of a present invention.

In at least some instances, it may be desirable for the BTE hearing assistance device 100 to wirelessly communicate with devices other than the cochlear stimulator 200. Examples of such auxiliary devices include, but are not limited to, remote controls, fitting apparatus, music players, mobile phones and a contra-lateral hearing aid (or other hearing assistance device). Such communication may be accomplished in a variety of ways. For example, communication by way of the data transmitter 116 and antenna 118 may be time multiplexed. Alternatively, and referring to FIG. 6, the exemplary BTE hearing assistance device 100*a* is essentially identical to BTE hearing assistance device 100 and similar elements are represented by similar reference numerals. The BTE hearing assistance device 100*a* may be used in place of the BTE hearing assistance device 100 in the system 10 in the manner described above. Here, however, an auxiliary transmitter/receiver 116*a* and antenna 118*a* create a second wireless link with an auxiliary device. For example, the wireless link created with the transmitter 116 and antenna 118 could operate at a first frequency (e.g., 13 MHz) and the transmitter/receiver 116*a* and antenna 118*a* could operate at a second frequency (e.g., 10.6 MHz) to create a pair of high bandwidth wireless links. Electrical impulses corresponding to sound are processed by the sound processor 106 for transmission to the cochlear stimulator 200 in the manner described above, while control signals from a remote control or fitting apparatus are used to adjust the functionality of the BTE hearing assistance device 100 in conventional fashion.

Figure 7:
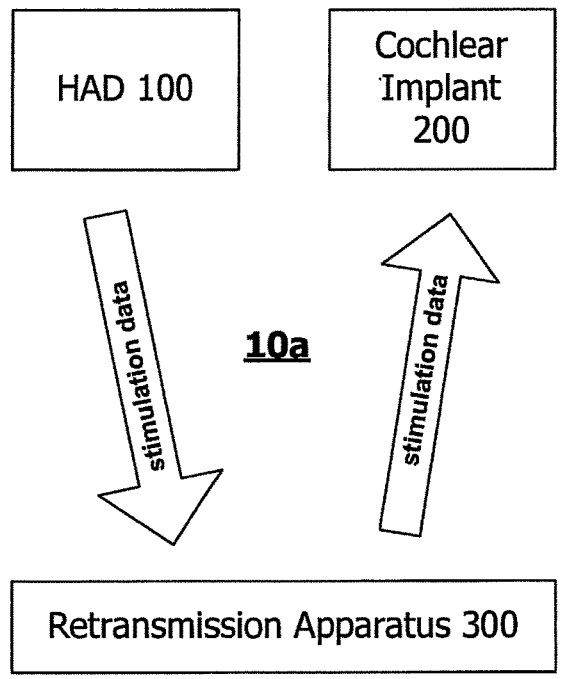
FIG. 7 is a block diagram showing components of an ICS system in accordance with one embodiment of a present invention.

There may be some instances where various factors, such as the location of the components relative to one another on the user's head, the size of the hearing assistance device (such as a BTE, RIC, ITC and CIC hearing assistance devices), and/or the power requirements of the hearing assistance device, make direct data transmission from the hearing assistance device to the implanted cochlear stimulator less than optimal. Here, a retransmission apparatus may be used to receive stimulation data from the hearing assistance device and to transmit that stimulation data to an implanted cochlear stimulator. One example of a system that includes such a retransmission apparatus is generally represented by reference numeral 10a in FIG. 7. The elements of system 10a are essentially identical to system 10 and similar elements are represented by similar reference numerals. For example, system 10a includes a BTE hearing assistance device 100 (or other external hearing assistance device) and a self-powered implantable cochlear simulator 200. The BTE hearing assistance device 100 creates stimulation data that is supplied to the cochlear simulator 200 by way of a wireless link. Here, however, the BTE hearing assistance device 100 transmits the stimulation data to a retransmission apparatus 300 and the retransmission apparatus transmits the stimulation data to the cochlear simulator 200. There is no headpiece in system 10a and, in particular, the retransmission apparatus is not a headpiece or an otherwise head-mounted device. The transmissions may occur at different frequencies such as, for example, 2.4 GHz from the BTE hearing assistance device 100 to the retransmission apparatus 300 and 49 MHz from the retransmission apparatus 300 to the cochlear simulator 200. The BTE hearing assistance device 100 may be a dual mode device that is capable of transmitting at one frequency when the retransmission apparatus 300 is employed and another frequency when it is not. Other systems may include a pair of hearing assistance devices that transmit stimulation data at different frequencies. Here, the user will select the appropriate hearing assistance device depending upon the intended mode of use.

The above-described arrangement is advantageous because the retransmission apparatus 300 need not be a head mounted device and, therefore, can include a much larger battery than a BTE hearing assistance device and, in turn, a sensitive receiver and a powerful transmitter.

Figure 8:
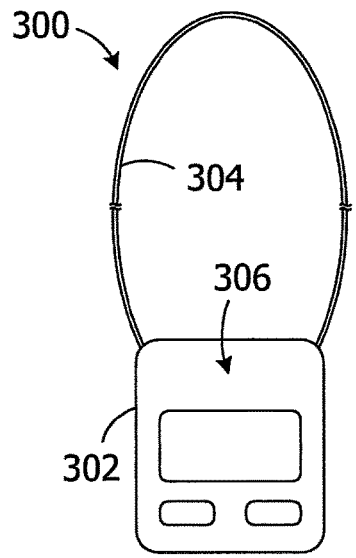
FIG. 8 is a plan view of a retransmission apparatus in accordance with one embodiment of a present invention.
Figure 9:
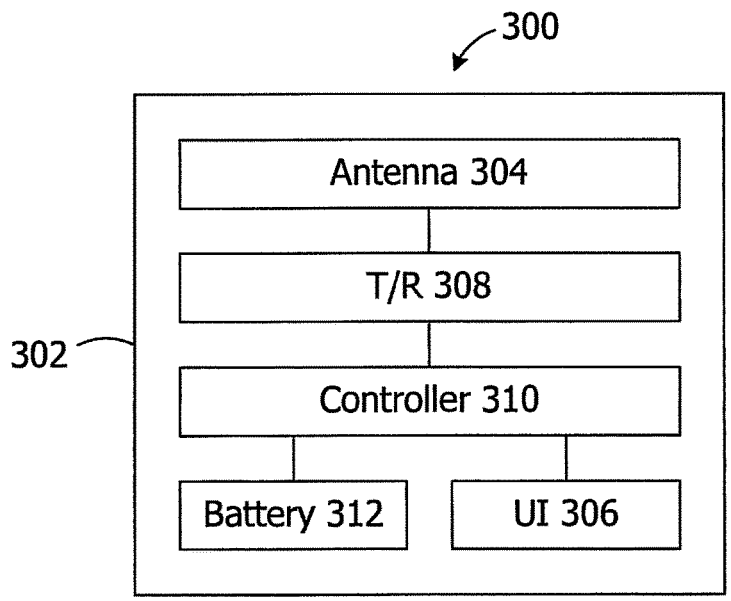
FIG. 9 is block diagram of a retransmission apparatus in accordance with one embodiment of a present invention.

Turning to FIGS. 8 and 9, the retransmission apparatus 300 includes a housing 302, an elongate antenna 304 that also functions as a lanyard so that the retransmission apparatus can be worn around the user's neck, and a user interface 306. A transmitter/receiver 308, controller 310 and battery 312 are located within the housing 302.

Figure 10:
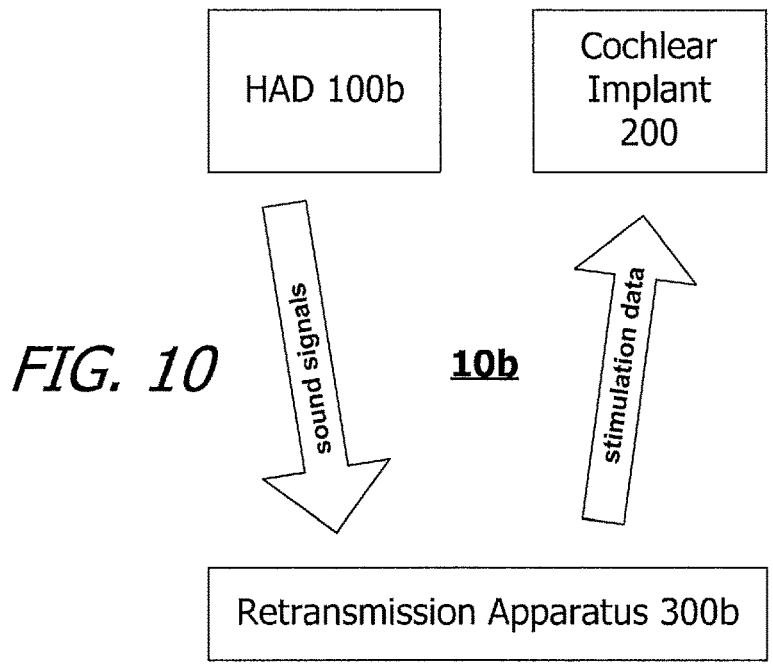
FIG. 10 is a block diagram showing components of an ICS system in accordance with one embodiment of a present invention.

Another exemplary system that employs a retransmission apparatus is generally represented by reference numeral 10b in FIG. 10. System 10b is substantially similar to system 10a and similar elements are represented by similar reference numerals. For example, there is no headpiece in system 10b. Here, however, the hearing assistance device 100b does not include sound processor circuitry. Instead of transmitting stimulation data, the hearing assistance device 100b transmits the electrical signals from a microphone to a retransmission apparatus 300b, which includes sound processor circuitry. The sound processor circuitry in the retransmission apparatus 300b converts the electrical signals from the microphone into stimulation data, and the retransmission apparatus transmits the stimulation data to the self-powered cochlear simulator 200 by way of a wireless data link.

Figure 11:
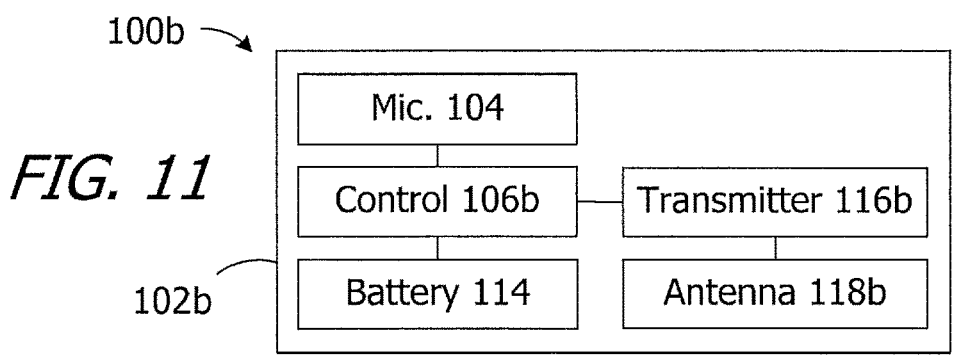
FIG. 11 is block diagram of a hearing assistance device in accordance with one embodiment of a present invention.
Figure 12:
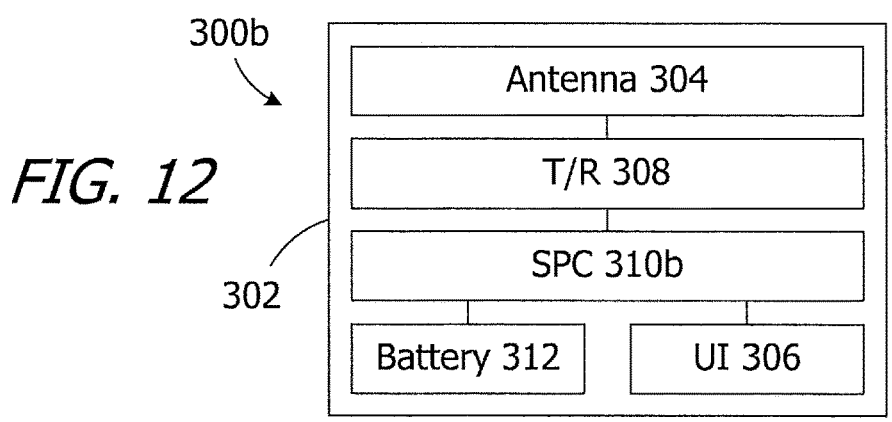
FIG. 12 is block diagram of a retransmission apparatus in accordance with one embodiment of a present invention.

Referring also to FIG. 11, the exemplary hearing assistance device 100b is a CIC device that includes a housing 102b configured to fit within the ear canal, a microphone 104, control circuitry 106b, a battery 114 and data communication apparatus (e.g., a transmitter 116b and an antenna 118b) that establishes a wireless data link with the retransmission apparatus 300b. In some implementations, a speaker may be provided. BTE and ITC hearing assistance devices may also be employed. The hearing assistance device 100b does not include circuitry that generates stimulation data. Instead, the data transmitted by the communication apparatus is the electrical signals from the microphone 104. Turning to FIG. 12, the exemplary retransmission apparatus 300b includes a housing 302, an antenna 304 that also functions as a lanyard, and a user interface 306. A transmitter/receiver 308, sound processing circuitry 310 and battery 312 are located within the housing 302. The electrical signals from the microphone 104, which are received by way of the antenna 304 and transmitter/receiver 308, are processed by the sound processing circuitry 310b in the manner described above with reference to sound processing circuitry 106. The resulting stimulation data is transmitted by retransmission apparatus 300b to the cochlear simulator 200. The respective transmissions from the hearing assistance device 100b to the retransmission apparatus 300b and from the retransmission apparatus 300b to the cochlear simulator 200 may occur at different frequencies (e.g., 2.4 GHz and 49 MHz).

Some systems in accordance with the present inventions may be configured to operate despite the fact that the implantable cochlear stimulator battery is not functioning properly. For example, the implantable cochlear stimulator battery may be a primary battery that has been fully discharged, a rechargeable battery that has been fully discharged and is unable to recharge due to battery failure or lack of a recharger, or a battery that has simply failed for some other reason. One example of such a system is generally represented by reference numeral 10c in FIG. 13. The exemplary ICS system 10c includes the external BTE hearing assistance device 100 (described above) and an implantable cochlear simulator 200a, and those are the only two components that are employed under the normal operating conditions described above with reference to ICS system 10. In other implementations, RIC, ITC and CIC hearing assistance devices may be employed. Briefly, the hearing assistance device 100 supplies stimulation data, but not power, to the cochlear simulator 200a by way of a wireless link and the cochlear simulator is powered by its own battery. Here, however, the system 10c also includes an external head mountable power supply 400 that is used to supply power to the cochlear simulator 200a, by way of a wireless power link, in those instances where the cochlear simulator battery is unable to power the cochlear stimulator.

Figure 13:
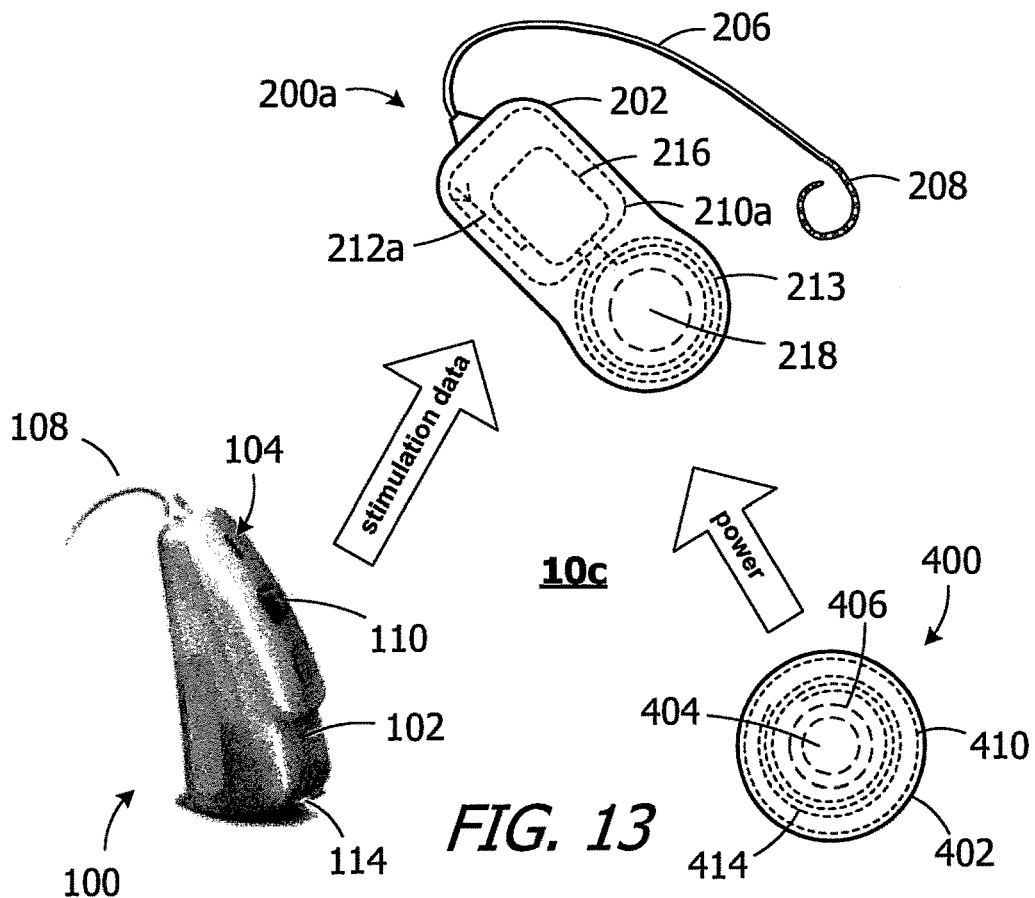
FIG. 13 is a plan view showing components of an ICS system in accordance with one embodiment of a present invention.
Figure 14:
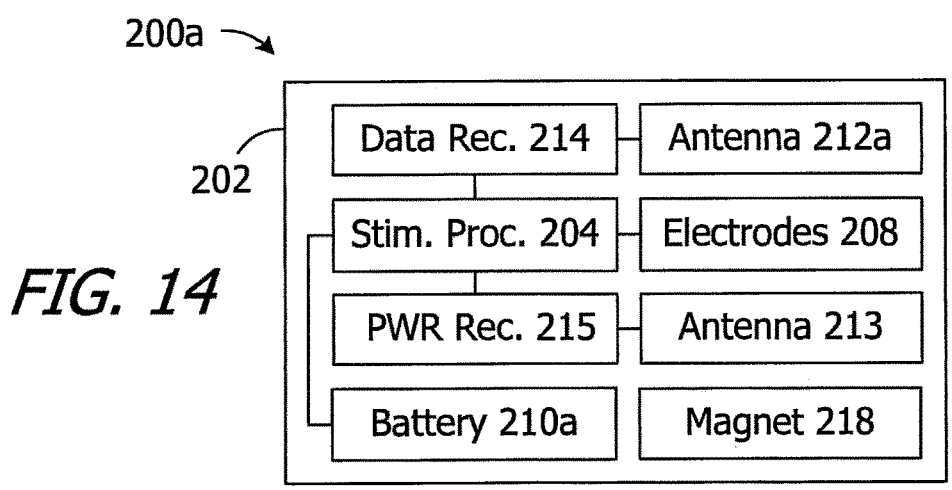
FIG. 14 is a block diagram of an implantable cochlear stimulator in accordance with one embodiment of a present invention.

The implantable cochlear simulator 200a is substantially similar to stimulator 200 and similar elements are represented by similar reference numerals. For example, as illustrated in FIGS. 13 and 14, the exemplary cochlear stimulator 200a includes a flexible housing 202, an internal stimulation processor 204, a cochlear lead 206 with an electrode array 208, a battery 210a (high energy primary or rechargeable), and a data receiver apparatus with a data antenna 212a and a data receiver 214. Here, however, a power receiver apparatus with a power antenna 213 and a power receiver 215. The stimulation processor 204 and the receivers 214 and 215 may be located on a common circuit board 216, or on separate boards. A positioning magnet 218 or other positioning device is adjacent to the power antenna 213. The antenna 212a and receiver 214 receive stimulation data from the hearing assistance device 100. The antenna 212a may be a coil antenna that is inductively coupled to the coil antenna 118 of the hearing assistance device 100. The data receiver apparatus may be, for example, an NFMI data receiver apparatus or an RF data receiver apparatus.

Figure 15:
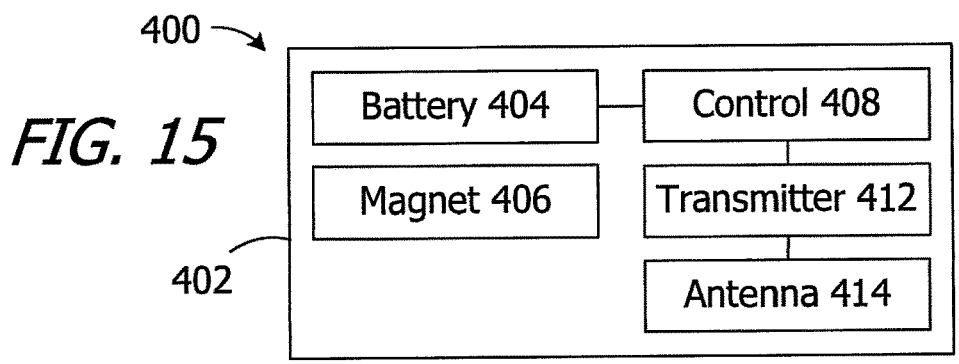
FIG. 15 is a block diagram of a power supply in accordance with one embodiment of a present invention.
Figure 16:
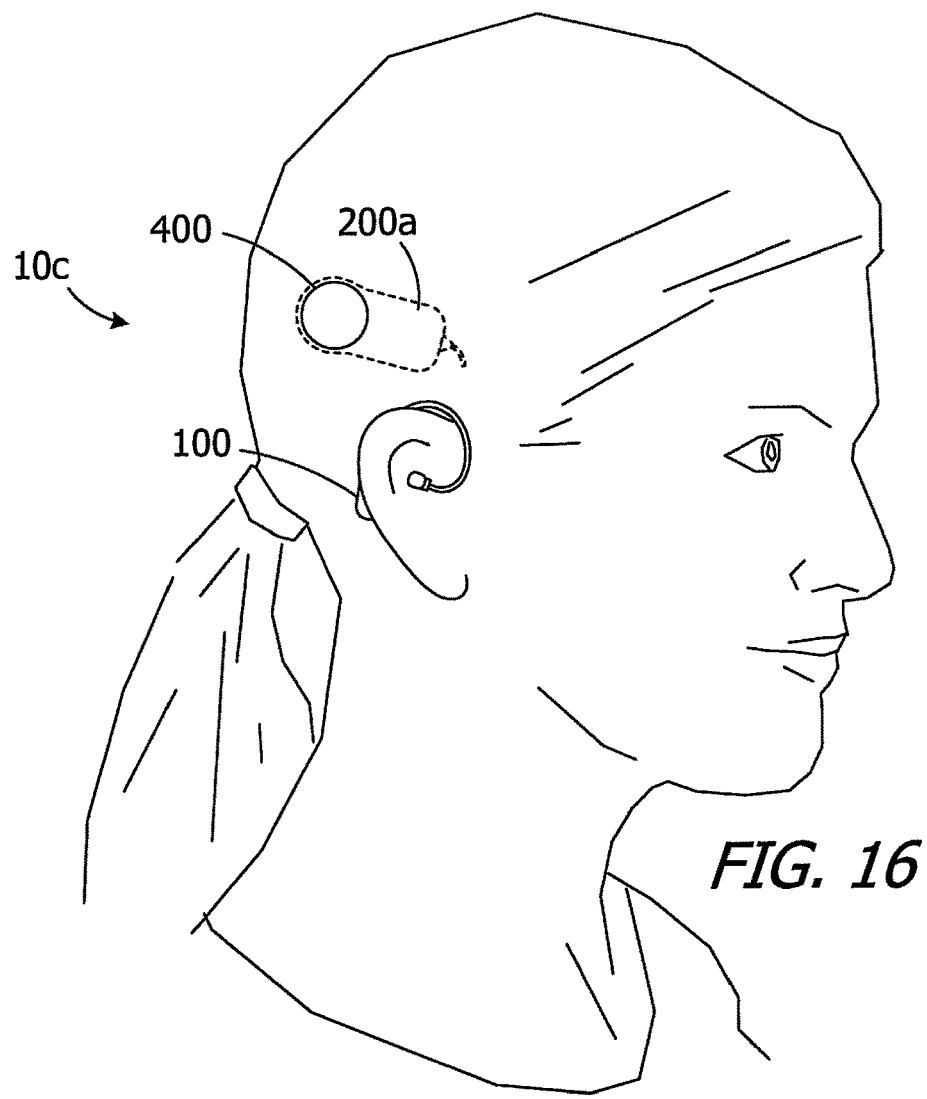
FIG. 16 is a side view showing the ICS system as illustrated in FIGS. 13-15 in use.

As illustrated in FIGS. 13 and 15, the exemplary external head mountable power supply (or "headpiece power supply") 400 includes a housing 402, a battery 404 (primary or secondary), a positioning magnet 406 that is attracted to the positioning magnet 218 of the cochlear stimulator 200a, power control circuitry 408 on a circuit board 410, a power transmission apparatus including a transmitter 412 that drives a coil antenna 414 (or other suitable antenna). The power control circuitry 410 controls the flow of power from the battery 404 to the transmitter 412 and coil antenna 414. In the illustrated embodiment, the transmitter 412 and antenna 414 generate a carrier with no data and form a close coupled inductive link with the power receiver antenna 213 of the cochlear stimulator 200*a*. The housing 402 includes a battery replacement door (not shown) so that the battery 404 may be removed and replaced as necessary. Alternatively, the secondary battery may be permanently housed within the housing and the door may be omitted. Such a head mountable power supply may be placed in a battery charger as necessary. In the illustrated implementation, there is no on/off switch and the power supply 400 operates so long as the battery 404 is not fully discharged. An on/off switch may be provided in other implementations. A low power indicator such as an LED may be provided in some implementations. With respect to power transmission level, which is typically a function of the thickness of the skin between the power supply 400 and the cochlear stimulator 200*a*, the power level may be preset as it is in the illustrated implementation. In others, a small knob may be provided that allows the power level to be adjusted during the fitting process.

The power supply 400 is used solely to supply power to the cochlear stimulator 200*a* and does not transmit cochlear stimulation data. To that end, the power supply 400 does not include a microphone or sound processor circuitry. The power supply 400 also does not communicate with the hearing assistance device 100 and there is no cable connecting the power supply to the hearing assistance device. It should also be noted that the present head mountable power supply is commensurate in size and shape with a conventional ICS headpiece (e.g., is between about 0.25 inch and 3 inches in diameter in some implementations and between about 0.5 inch and 1.5 inch in other implementations) and is not a BTE device or other hearing assistance device, nor is it part of a BTE device or other hearing assistance device.

The circuitry of the cochlear stimulator 200*a* includes apparatus (e.g., switches and/or fuses) that may be used to electrically disconnect the battery 210*a* from some (e.g., the stimulation processor 204) or all of the remainder of the cochlear stimulator. Such apparatus may be controlled by the hearing assistance device 100. Power for operation of the cochlear stimulator 200*a* may be provided by the power supply 400, and the cochlear stimulator will operate in the manner described above. In other words, the cochlear stimulator 200*a* is operable in a first stimulation mode (i.e., it converts stimulation data from the hearing assistance device 100 into stimulation signals that stimulate the electrodes in the array 208) where the battery 210*a* supplies operational power, and is also operable in a second stimulation mode (i.e., it converts stimulation data from the hearing assistance device 100 into stimulation signals that stimulate the electrodes in the array 208) where the battery 210*a* is disconnected and the power supply 400 supplies operational power. The circuitry of the cochlear stimulator 200*a* may also be used to recharge the battery 210*a* with power from the power supply 400.

In at least some implementations, the cochlear stimulator 200*a* may provide the power supply 400 with information that can be used to, for example, optimize power transmission to the cochlear stimulator by adjusting the transmission level to a level below the maximum level, when possible, to extend the life of the battery 404. For example, information concerning the current supply voltage of the cochlear stimulator 200*a* may be used by the power supply 400 to modulate power to the cochlear stimulator in real time. The information may be provided in a variety of ways. For example, a low data rate back telemetry link from the cochlear stimulator 200*a*, which is indicative of the tank voltage of the implant (e.g., a single bit which indicates whether the tank voltage is at or below a predetermined level), may be used by the power control circuitry 408 to modulate power from the power supply 400. Alternatively, the cochlear stimulator 200*a* may be configured to alter its effective impedance as a function of the tank voltage. The effective impendence can be detected by the power control circuitry 408 and used to modulate power from the power supply 400.

In those instances where the cochlear stimulator 200*a* of the exemplary system 10*c* is being powered by the power supply 400 (FIG. 16), the hearing assistance device 100 is positioned behind the ear and the power supply 400 is positioned over the implanted cochlear stimulator 200*a*. The power supply 400 is not connected to the hearing assistance device 100 by a cable. Nor is there wireless communication between the hearing assistance device 100 and the power supply 400. The attraction of the power supply magnet 406 to the stimulator magnet 218 aligns the power supply antenna 414 with the cochlear stimulator power receiver antenna 213. Power from the power supply 400 is supplied to the implanted cochlear stimulator 200*a*. The hearing aid microphone 104 picks up ambient sound pressure waves and converts them into electrical signals. The electrical signals are the processed by the sound processor circuitry 106 and converted to stimulation data (e.g., a pulse sequence having varying pulse widths and/or amplitudes). The hearing aid data transmitter 116 and antenna 118 establish a wireless link with the cochlear stimulator data antenna 212*a* and receiver 214 and transmit the stimulation data, but not power, to the implantable cochlear simulator 200*a*. The antenna 212*a* and receiver 214 receive the stimulation data and send the data to the stimulation processor 204 which, in turn, converts the data into stimulation signals that stimulate the electrodes in the array 208. The electrode array 208 electrically stimulates the auditory nerve inside the cochlea, thereby providing the user with sensory input that is a representation of external sound waves which were sensed by the microphone 104.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A hearing assistance system, comprising:
  an implantable cochlear stimulator including a battery, an electrode array, a stimulation data receiver apparatus, and a stimulation processor operably connected to the stimulation data receiver apparatus and to the electrode array;
  a hearing assistance device including a battery, sound processor circuitry that converts electrical signals from a microphone into stimulation data, and a data communication apparatus configured to wirelessly transmit the stimulation data; and
  a retransmission apparatus, including a data communication apparatus, that wirelessly receives the stimulation data and wirelessly transmits the stimulation data to the implantable cochlear stimulator;
wherein the system does not include a headpiece.

2. A hearing assistance system as claimed in claim 1, wherein the implantable cochlear stimulator does not include sound processor circuitry.

3. A hearing assistance system as claimed in claim 1, wherein the hearing assistance device comprises a behind-the-ear hearing assistance device.

4. A hearing assistance system as claimed in claim 1, wherein the hearing assistance device includes the microphone.

5. A hearing assistance system as claimed in claim 1, wherein the data communication apparatus of the hearing assistance device is configured to wirelessly transmit the stimulation data at a first frequency and the data communication apparatus of the retransmission apparatus is configured to wirelessly transmit the stimulation data at a second frequency that is different than the first frequency.

6. A hearing assistance system as claimed in claim 1, wherein the retransmission apparatus includes a battery.

7. A hearing assistance system as claimed in claim 1, wherein the retransmission apparatus includes a housing and an elongate loop-shaped antenna located outside the housing.

8. A hearing assistance system as claimed in claim 1, wherein the hearing assistance device does not supply power to the implantable cochlear stimulator.

9. A hearing assistance system as claimed in claim 1, wherein the data communication apparatus of the hearing assistance device comprises a transmitter and an antenna.

10. A hearing assistance system as claimed in claim 1, wherein the implantable cochlear stimulator does not include a magnet.

11. A hearing assistance system, comprising:
an implantable cochlear stimulator including a battery, an electrode array, a stimulation data receiver apparatus, and a stimulation processor operably connected to the stimulation data receiver apparatus and to the electrode array;
a hearing assistance device, including a battery, a microphone that converts sound pressure waves into electrical signals, and data communication apparatus that wirelessly transmits the electrical signals; and
a retransmission apparatus, which is not configured to be mounted on the user's head, including a data communication apparatus and sound processor circuitry, that wirelessly receives electrical signals from the hearing assistance device, converts the electrical signals from the microphone into stimulation data, and wirelessly transmits the stimulation data to the implantable cochlear stimulator.

12. A hearing assistance system as claimed in claim 11, wherein the hearing assistance device comprises a CIC hearing assistance device.

13. A hearing assistance system as claimed in claim 11, wherein the data communication apparatus of the hearing assistance device comprises a transmitter and an antenna.

14. A hearing assistance system as claimed in claim 11, wherein the hearing assistance device does not include sound processor circuitry.

15. A hearing assistance system as claimed in claim 11, wherein the hearing assistance device does not supply power to the implantable cochlear stimulator.

16. A hearing assistance system as claimed in claim 11, wherein the data communication apparatus of the hearing assistance device is configured to wirelessly transmit the electrical signals at a first frequency and the data communication apparatus of the retransmission apparatus is configured to wirelessly transmit the stimulation data at a second frequency that is different than the first frequency.

17. A hearing assistance system as claimed in claim 11, wherein the retransmission apparatus includes a housing and an elongate loop-shaped antenna located outside the housing.

18. A hearing assistance system as claimed in claim 11, wherein the implantable cochlear stimulator does not include a magnet.

19. A hearing assistance system, comprising:
an implantable cochlear stimulator including a battery, an electrode array, a stimulation data receiver apparatus, and a stimulation processor operably connected to the stimulation data receiver apparatus and to the electrode array, and not including sound processor circuitry;
a hearing assistance device, including a battery, a microphone that converts sound pressure waves into electrical signals, and data communication apparatus that wirelessly transmits the electrical signals; and
a retransmission apparatus, including a data communication apparatus and sound processor circuitry, that wirelessly receives electrical signals from the hearing assistance device, converts the electrical signals from the microphone into stimulation data, and wirelessly transmits the stimulation data to the implantable cochlear stimulator.

* * * * *